United States Patent [19]

Guilbaud et al.

[11] 4,011,594
[45] Mar. 15, 1977

[54] WELDING MASK WINDOW DOOR AUTOMATIC OPERATION

[76] Inventors: Antoine L. Guilbaud, c/o George Spector, 3615 Woolworth Building, 233 Broadway; George Spector, 3615 Woolworth Building, 233 Broadway, both of New York, N.Y. 10007

[22] Filed: Sept. 29, 1975

[21] Appl. No.: 617,326

[52] U.S. Cl. .................................................. 2/8
[51] Int. Cl.² .................................... A61F 9/06
[58] Field of Search ............. 2/8, 14 R, 14 J, 14 H, 2/14 G, 9

[56] References Cited
UNITED STATES PATENTS

| | | | |
|---|---|---|---|
| 1,643,509 | 9/1927 | Moran | 2/14 J |
| 2,154,774 | 4/1939 | Rienacker et al. | 2/8 |
| 2,487,183 | 11/1949 | Rohlf | 2/8 |
| 2,660,728 | 12/1953 | Thornton | 2/14 J |
| 2,678,369 | 5/1954 | Van Hook | 2/8 X |

FOREIGN PATENTS OR APPLICATIONS

| | | | |
|---|---|---|---|
| 455,647 | 1/1928 | Germany | 2/8 |
| 292,940 | 8/1953 | Switzerland | 2/8 |

*Primary Examiner*—Werner H. Schroeder
*Assistant Examiner*—Peter Nerbun

[57] ABSTRACT

An improved welding mask having a tinted window door that automatically closes as soon as a welding rod strikes an object that is intended to be welded, and wherein the door automatically opens and all electric current is shut the moment the welding arc is broken; the mask including an electrical circuit for accomplishing the same, the circuit including a transformer, relay and rectifier for activating a pair of door operating relays at opposite sides of the door, and the circuit extending through the welding torch and the work.

3 Claims, 8 Drawing Figures

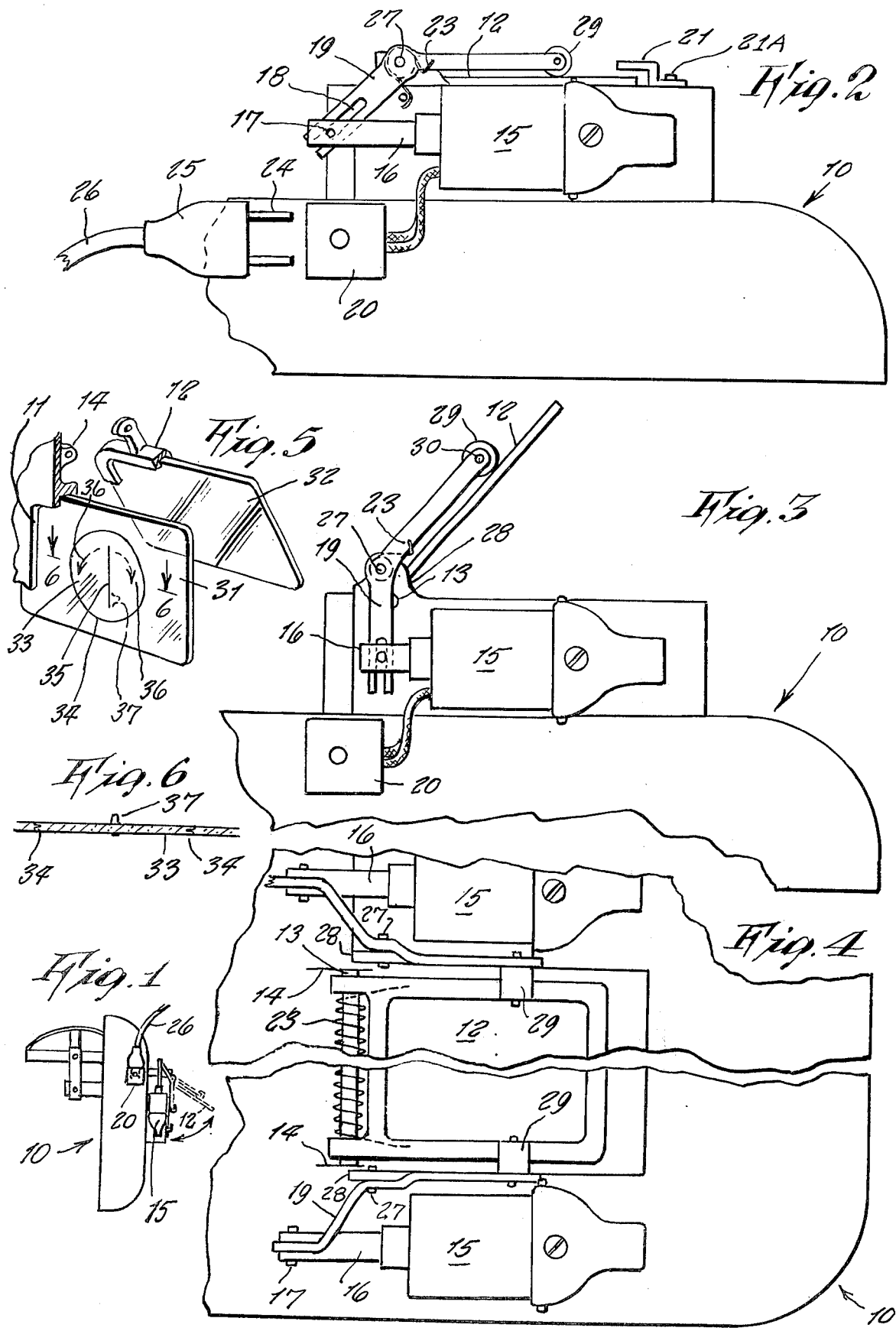

WELDING MASK WINDOW DOOR AUTOMATIC OPERATION

A principle object of the present invention is to provide a welding mask wherein a welder will have more precision for the first strike and he will have his two hands free for action.

Another object is to provide a welding mask wherein the mask window door automatically pivots into a closed position as soon as a welding rod strikes the object that is intended to be welded, so that the welder can observe the work directly through the open window up till the moment that the welding operation starts, so to see that his welding torch is in a proper relation to the work, and the window door is thus closed the moment that the welding is started, thus protecting his eyes from the moment that the welding operation begins.

Yet another object is to provide a welding mask wherein the instant that the welding arc is broken after a welding operation, all the electrical current is automatically shut off for purpose of safety, and at a same time the window door flies back open so the welder can see the work through the open window.

Still another object is to provide a welding mask wherein the same can be selectively adjusted so to use like a conventional welding mask without the door closing and opening automatically.

Other objects are to provide a welding mask which is simple in design, inexpensive to manufacture, rugged in construction, easy to use and efficient in operation.

These and other objects will be readily evident upon a study of the following specification and the accompanying drawings wherein:

FIG. 1 is a side view of a welding helmet that incorporates the present invention.

FIG. 2 is an enlarged side view detail thereof shown with the window thereof in a closed position.

FIG. 3 is a view similar to FIG. 2, and showing the window flipped open.

FIG. 4 is a fragmentary front elevation view of the helmet.

FIG. 5 shows a modified additional feature included in the invention wherein a clear window behind the smoked window including a rotatable transparent lightly smoke tinted glass with an opaque guide line inscribed thereupon so to guide the operator in welding a straight line in any direction if he maintains his hand steady once it is aligned with the welding path of the work prior to the smokey glass closing.

FIG. 6 is an enlarged cross sectional view taken on line 6—6 of FIG. 5.

Figure 7:
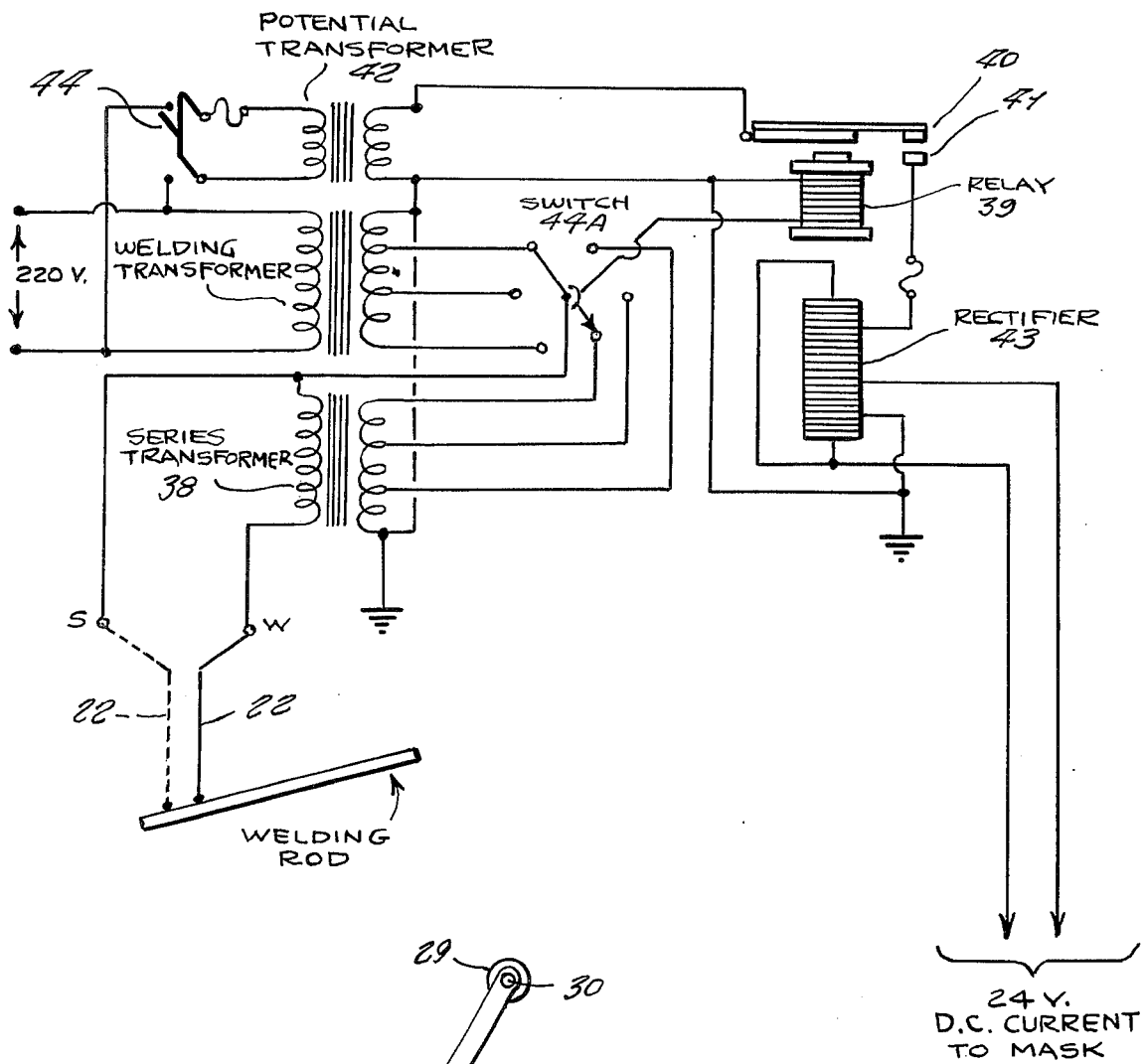

FIG. 7 is an electric circuit of the invention.

Figure 8:
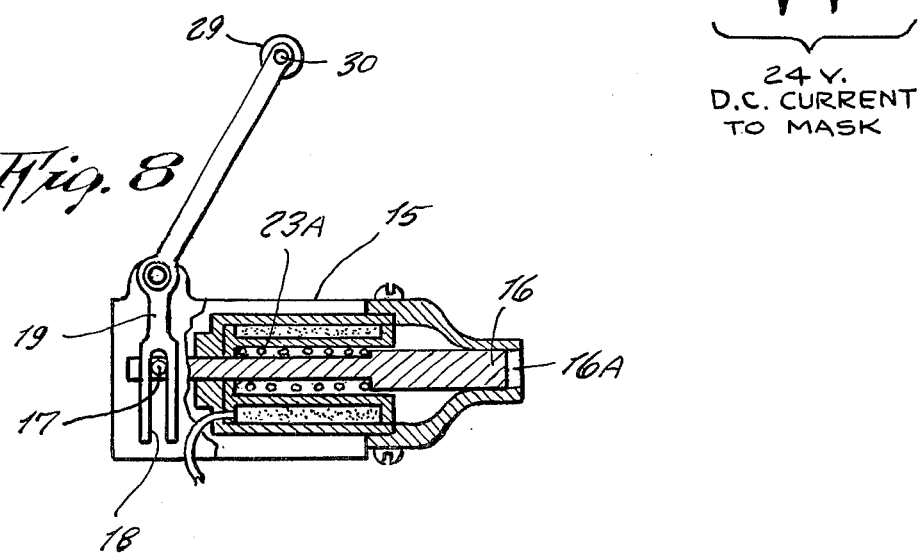

FIG. 8 is a side cross sectional view of the window pivoting mechanism.

Referring now to the drawings in detail, the reference numeral 10 represents a welding mask according to the present invention wherein the mask includes an observation window opening 11 on its front side so that a welder wearing the mask can look out through it. The window opening 11 can be selectively kept opened or closed by means of a door 12 that is pivotable within the window; the door consisting of a framed, deeply tinted transparent shade so to filter out the harmful rays of a welding arc. The door is firmly secured to a shaft 13 pivotable in stationary bearings 14, and the shaft being rotatable by a 24 volts D.C. solenoid relays 15 at each side of the shaft. Each solenoid relay has a plunger 16 with cross pin 17 that rides in a slot 18 of a fork 19.

The welding mask has a socket 20 secured thereupon for purpose of bring electrical power to the operating relay 15, the socket 20 being engagable by the prongs 24 of a plug 25 on an end of an extension cord 26.

An electrical circuit 21 of the present invention includes a transformer and a rectifier that comprise heavy equipment so are not mounted on the mask.

In operative use, as soon as the rod strikes the object that is to be welded, a complete electrical circuit is made in a primary of a series transformer 38, induces a voltage in the secondary winding which is provided with taps proportional to the amperes used controlled by dial 44A causing a current to flow in the secondary circuit in order to operate a relay 39 which closes its contacts 40 and 41 thus supplying A.C. current from a potential transformer 42 to a rectifier 43 which energizes the window door operating relays 15 with D.C. current which closes the window door. The D.C. flexible cable is to be secured to the welder's waist in order to avoid unnecessary pulling force on the mask. As soon as the welding arc is broken, all the electrical current is shut off, and the window door then automatically flies back open by means of a tension coil spring 23.

The two window door operating relays 15 are used, one being on each side of the mask. These relays may be built to operate either in parallel or in series electric circuit with suitable wiring. When desired, the mask can be used in a manner similarly to a conventional mask; on such occasion the D.C. flexible cable being disconnected, and the window door being locked in closed position by means of a clamp 21 pivotable about a pin 21A and transferring the work cable 22 from the bolt W to the bolt S after the potential transformer switch 44 is opened.

It is to be further noted that a relay 15 is positioned adjacent each vertical side edge of the window, and the fork 19 actuated by each relay is pivotable about the pivot pin 27 supported in stationary lugs 28 formed on a front of the helmet. The coil spring 23 is mounted around the pivot shaft 13, and serves to bias the door in an opened position while the relays serve to electrically close the doors. Rollers 29 pivotable on pins 30 affixed at the end of the forks 19 ride on the outer side of the door frame, as shown in FIGS. 2, 3 and 4. The lower end of the relay casing is open at 16A to reduce resistance to movement of pin 16.

In FIGS. 5 and 6, a modified design of the invention, including a transparent lightly smoke tinted glass 31 is affixed to the mask behind the tinted shade 32 of the door 12; the glass 31 having a rotatable transparent circular glass 33 supported in a circular groove 34. The glass 33 has an opaque straight guide line 35 engraved thereupon. In use, the glass 33 is rotatable in either direction as indicated by arrows 36 so that the guide line 35 can be aligned (before door 12 is closed) with a proposed or intended line of welding to be done on the work. Then after the door 12 is closed, and by maintaining his hand steady, the welder can follow the guide line with his welding torch so to accomplish a straight weld. A protrusion 37 on glass 33 serve as a knob so to easily rotate it. The glass 33 is smaller in vertical dimension than the door 12 whereby it will provide some unobstructed opening when the door 12 is open.

While various changes may be made in the detail construction, it is understood that such changes will be within the spirit and scope of the present invention as is defined by the appended claims.

What is claimed is:

1. A welding mask having a door pivotally mounted on a door frame surrounding an opening said door being pivotally movable between an opened and a closed position, said door having a transparent, tinted window whereby a user can look through said door at strong light when said door is in closed position, in combination with electrically operated means mounted on said frame for pivoting said door from the open to the closed position, said means comprising solenoid relay means supported on said frame, a lever, said solenoid relay having a plunger pivotally engaging one end of said lever mounted rotatably on said frame side including an opposite end of said lever carrying a roller that bears against the front of said door to urge said door pivotally closed, when said relays are electrically actuated, including a spring biasing said door the open position.

2. The combination as set forth in claim 1 wherein an upper end of said door is secured to a horizontal shaft pivotally about stationary bearings, said spring being a coil wound around said shaft and normally urging said door towards the open position in combination with an electric circuit including a welding torch which actuates said relays upon contact with the work.

3. The combination as set forth in claim 2 including a second transparent window mounted in the frame in said opening spaced inwardly from the first said window and including a central portion rotatable about a central axis normal to said windows, said portion having a straight guide line, said frame including a movable clamp mounted on the frame adjacent the door adapted to retain the door in closed position against the action of the spring, particularly when the solenoid relays are not electrically actuated.

* * * * *